United States Patent
De Wilde et al.

(10) Patent No.: US 10,632,093 B2
(45) Date of Patent: *Apr. 28, 2020

(54) METHOD FOR IMPROVING RECOGNITION AND/OR WORKING MEMORY IN HYPERPHENYLALANIMENIA AND PHENYLKETONURIA PATIENTS

(71) Applicant: N.V. Nutricia, Zoetermeer (NL)

(72) Inventors: Mattheus Cornelis De Wilde, Utrecht (NL); Danielle Stefanie Counotte, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/770,116

(22) PCT Filed: Oct. 24, 2016

(86) PCT No.: PCT/NL2016/050735
§ 371 (c)(1),
(2) Date: Apr. 20, 2018

(87) PCT Pub. No.: WO2017/069632
PCT Pub. Date: Apr. 27, 2017

(65) Prior Publication Data
US 2018/0311197 A1    Nov. 1, 2018

(30) Foreign Application Priority Data

Oct. 23, 2015    (WO) ................ PCT/NL2015/050740

(51) Int. Cl.
| | | |
|---|---|---|
| *A61K 31/202* | (2006.01) | |
| *A61K 31/355* | (2006.01) | |
| *A61K 31/7072* | (2006.01) | |
| *A61K 31/714* | (2006.01) | |
| *A61K 33/04* | (2006.01) | |
| *A23L 33/15* | (2016.01) | |
| *A23L 33/175* | (2016.01) | |
| *A23L 33/12* | (2016.01) | |
| *A61K 31/593* | (2006.01) | |
| *A61K 31/4415* | (2006.01) | |
| *A61K 31/592* | (2006.01) | |
| *A61K 31/7068* | (2006.01) | |
| *A23L 33/115* | (2016.01) | |
| *A61K 31/4172* | (2006.01) | |
| *A61K 45/06* | (2006.01) | |

(Continued)

(52) U.S. Cl.
CPC .......... *A61K 31/202* (2013.01); *A23L 33/115* (2016.08); *A23L 33/12* (2016.08); *A23L 33/15* (2016.08); *A23L 33/175* (2016.08); *A61K 31/122* (2013.01); *A61K 31/14* (2013.01); *A61K 31/198* (2013.01); *A61K 31/341* (2013.01); *A61K 31/355* (2013.01); *A61K 31/375* (2013.01); *A61K 31/4172* (2013.01); *A61K 31/4415* (2013.01); *A61K 31/455* (2013.01); *A61K 31/525* (2013.01); *A61K 31/59* (2013.01); *A61K 31/592* (2013.01); *A61K 31/593* (2013.01); *A61K 31/675* (2013.01); *A61K 31/7068* (2013.01); *A61K 31/7072* (2013.01); *A61K 31/714* (2013.01); *A61K 33/04* (2013.01); *A61K 38/02* (2013.01); *A61K 45/06* (2013.01); *A23V 2002/00* (2013.01); *A61K 2300/00* (2013.01)

(58) Field of Classification Search
CPC .............. A61K 31/202; A61K 31/4415; A61K 31/714; A61K 31/525; A61K 31/7068; A61K 31/593; A61K 31/7072; A61K 31/592; A61K 31/341; A61K 31/355; A61K 31/198; A61K 31/4172; A61K 31/455; A61K 31/375; A61K 31/14; A61K 31/122; A61K 31/59; A61K 31/675; A61K 33/04; A61K 45/06; A61K 38/02; A61K 2300/00; A23L 33/115; A23L 33/15; A23L 33/175; A23L 33/12
See application file for complete search history.

(56) References Cited

U.S. PATENT DOCUMENTS

| | | |
|---|---|---|
| 4,252,822 A | 2/1981 | Berry |
| 7,384,981 B2 | 6/2008 | Kiliaan et al. |

(Continued)

FOREIGN PATENT DOCUMENTS

| | | | |
|---|---|---|---|
| CN | 104012659 A | | 9/2014 |
| EP | 1 800 675 A1 | * | 6/2007 |

(Continued)

OTHER PUBLICATIONS

Start ("Treating phenylketonuria by a phenylalanine-free diet," Prof Care Mother Child, 1998, 8(4) abstract), 1998.*

(Continued)

*Primary Examiner* — Blessing M Fubara
(74) *Attorney, Agent, or Firm* — Gilberto M. Villacorta; Sunit Talapatra; Foley & Lardner LLP

(57) ABSTRACT

The invention pertains to the use of a composition in the manufacture of a product or method for therapeutically improving, promoting, restoring or maintaining recognition and/or working memory in a subject suffering from PKU and/or in a subject suffering from or at increased risk of impaired recognition and/or working memory associated with PKU, said composition comprising therapeutic amounts of: (i) at least one ω-3 polyunsaturated fatty acid (LCPUFA) selected from the group consisting of docosahexaenoic acid (DHA), eicosapentaenoic acid (EPA) and docosapentaenoic acid (DPA); (ii) choline, a choline salt and/or choline ester; and (iii) at least one B vitamin selected from the group consisting of vitamin B6, vitamin B12 and vitamin B9, including functional equivalents thereof, preferably vitamin B6 and/or vitamin B12, and functional equivalents thereof. The invention also pertains to a composition for use in such use or method.

19 Claims, 2 Drawing Sheets
Specification includes a Sequence Listing.

(51) Int. Cl.

| | |
|---|---|
| A61K 31/525 | (2006.01) |
| A61K 31/198 | (2006.01) |
| A61K 31/341 | (2006.01) |
| A61K 31/122 | (2006.01) |
| A61K 31/14 | (2006.01) |
| A61K 31/375 | (2006.01) |
| A61K 31/455 | (2006.01) |
| A61K 31/59 | (2006.01) |
| A61K 31/675 | (2006.01) |
| A61K 38/02 | (2006.01) |

(56) References Cited

U.S. PATENT DOCUMENTS

| | | | |
|---|---|---|---|
| 10,039,732 | B2 * | 8/2018 | Van Anholt .......... A61K 31/202 |
| 2005/0203053 | A1 | 9/2005 | Wurtman et al. |
| 2006/0247153 | A1 | 11/2006 | McMahon et al. |
| 2011/0009357 | A1 | 1/2011 | Hageman et al. |
| 2011/0105594 | A1 | 5/2011 | De Kort et al. |
| 2013/0136800 | A1 | 5/2013 | Gil Hernandez et al. |
| 2014/0066397 | A1 | 3/2014 | De Wilde et al. |
| 2018/0311196 | A1 | 11/2018 | Savelkoul et al. |

FOREIGN PATENT DOCUMENTS

| | | |
|---|---|---|
| EP | 1 800 675 A1 | 6/2007 |
| EP | 2 162 019 B1 | 3/2010 |
| WO | WO-98/08402 A1 | 3/1998 |
| WO | WO-00/06174 A1 | 2/2000 |
| WO | WO-02/088159 A1 | 11/2002 |
| WO | WO-2005/009349 A2 | 2/2005 |
| WO | WO-2006/072084 A2 | 7/2006 |
| WO | WO-2006/127620 A2 | 11/2006 |
| WO | WO-2007/073177 A2 | 6/2007 |
| WO | WO-2007/089703 A2 | 8/2007 |
| WO | WO-2009/002148 A1 | 12/2008 |
| WO | WO-2009/002165 A1 | 12/2008 |
| WO | WO-2009/002166 A1 | 12/2008 |
| WO | WO-2009/059306 A1 | 5/2009 |
| WO | WO-2011/119023 A1 | 9/2011 |
| WO | WO-2012/091542 A1 | 7/2012 |
| WO | WO-2012/125020 A1 | 9/2012 |
| WO | WO-2013/066151 A1 | 5/2013 |
| WO | WO-2013/066152 A1 | 5/2013 |
| WO | WO-2013/066165 | 5/2013 |
| WO | WO-2013/066167 | 5/2013 |
| WO | WO 2013/129914 A1 * | 9/2013 |
| WO | WO-2013/129931 A1 | 9/2013 |
| WO | WO-2013/133691 A1 | 9/2013 |
| WO | WO-2014/171813 A1 | 10/2014 |
| WO | WO 2014171813 A1 * | 10/2014 |
| WO | WO-2015/084161 | 6/2015 |
| WO | WO-2015/115885 A1 | 8/2015 |

OTHER PUBLICATIONS

Cooler system product published Apr. 2009 and submitted in IDS filed Jul. 10, 2019.*
Adamo, "Nutritional factors and aging in demyelinating diseases", Genes and Nutrition, 2013, vol. 9, 9 pages.
Adler-Abramovich et al., "Phenylalanine assembly into toxic fibrils suggests amyloid etiology in phenylketonuria", Nature Chemical Biology, 2012, 6 pages.
Anderson et al., "White matter pathology in phenylketonuria", Molecular Genetics and Metabolism, 2010, vol. 99, pp. S3-S9.
Broersen et. al., "A specific multi-nutrient diet reduces Alzheimer-like pathology in young adult AbetaPPswe/PS1dE9 mice", Journal of Alzheimer's Disease, 2013, vol. 33, pp. 177-190.
Bruinenberg et al., "A specific nutrient combination attenuates the reduced expression of PSD-95 in the proximal dendrites of hippocampal cell body layers in a mouse model of Phenylketonuria", Nutrients, 2016, vol. 8, 8 pages.
Dyer et al., "Evidence for central nervous system glial cell plasticity in Phneylketonuria", Journal of Neuropathology and Experimental Neurology, 1996, vol. 55, No. 7, pp. 795-814.
Hommes et al., "Turnover of the fast components of myelin and myelin proteins in experimental hyperphenylalaninaemia. Relevance to termination of dietary treatment in human phenylketonuria", Journal of Inherited Metabolic Disease, 1982, vol. 5, pp. 21-27.
International Search Report issued in International Patent Application No. PCT/NL2016/050733, dated Mar. 6, 2017.
International Search Report issued in International Patent Application No. PCT/NL2016/050734, dated Dec. 15, 2016.
International Search Report issued in International Patent Application No. PCT/NL2016/050735, dated Feb. 24, 2017.
Koletzko et al., Omega-3 LC-PUFA supply and neurological outcomes in children with Phenylketonuria (PKU), Journal of Pediatric Gastroenterology and Nutrition, 2009, vol. 48, Suppl. 1, pp. S2-S7.
Kono et al., "Diffusion-weighted MR imaging in patients with Phenylketonuria: relationship between serum Phenylalanine levels and ADC values in cerebral white matter", Radiology, 2005, vol. 236, pp. 630-636.
Macleod et al. "Nutritional management of Phenylketonuria", Annales Nestle, 2010, vol. 68, pp. 58-69.
Nutricia: "Souvenaid A food for special medical purposes that nutritionally supports memory function during the early stages of Alzheimer's disease", souvenaid.com.au, Mar. 2015, retrieved from the Internet: URL:http://web.archive.org/web/20150328111033/https://www.souvenaid.com.au/uploadedFiles/souvenaid_australia/Content/Souvenaid/Souvenaid_Information_Sheet/Souvenaid%20fact%sheet%20-%20consumer.pdf.
White et al., "Age-related working memory impairments in children with prefrontal dysfunction associated with phenylketonuria", Journal of the International Neuropsychological Society, 2002, vol. 8, pp. 1-11.
White et al., "White matter integrity and executive abilities following treatment with tetrahydrobiopterin (BH4) in individuals with phenylketonuria", Mol Genet Metab., Nov. 2013, vol. 110, No. 3, 15 pages.
Wurtman et al., "Synaptic proteins and phospholipids are increased in gerbil brain by administering uridine plus docosahexaenoic acid orally", Brain Research, 2006, vol. 1088, pp. 83-92.
Anonymous, Compound 'cocktail' improves brain function in rodents, Treatment is undergoing a clinical study in Alzheimer's patients, MIT, vol. 52, No. 10 Wednesday, Nov. 28, 2007.
Database GNPD [Online] MINTEL, Anonymous: "Cooler System", XP002723210, Sep. 2009, retrieved from www.gnpd.com.
De Waal et al., "The effect of souvenaid on functional brain network organization in patients with mild Alzheimer's Disease: a randomized controlled study", PLOS One, Jan. 2014, vol. 9, Issue 1, pp. 2-11.
Giovannini et al., "Phenylketonuria: nutritional advances and challenges", Nutrition & Metabolism, Feb. 3, 2012, vol. 9, No. 7, pp. 1-7.
Hampel et al., Total and Phosphorylated Tau Protein as Biological Markers of Alzheimer's Disease, Exp Gerontol. Jan. 2010; 45(1): 30.
Liang et al. "Phenylketonuria-related synaptic changes in a BTBR-pah enu2 mouse model", NeuroReport, 2011, vol. 22, No. 2, pp. 617-622.
Schef et al., "Glucose metabolism, gray matter structure, and memory decline in subjective memory impairment", Neurology, Sep. 25, 2012, vol. 79, pp. 1332-1339.
Schwab et al., "Functions of Nogo proteins and their receptors in the nervous system", Nature Reviews Neuroscience, Dec. 2010, vol. 11, pp. 799-811.
Silverman et al., Positron Emission Tomography in Evaluation of Dementia Regional Brain Metabolism and Long-term Outcome, JAMA, Nov. 7, 2001—vol. 286, No. 17.
Thoma-Worringer et al., "Gewinnung von Caseinomacropeptid durch Membranverfahren und technologischer Einsatz zur Steigerung der ernahrungsphysiologischen Funktionalitat von Milchprodukten", Chemie Ingenieur Technik, Sep. 1, 2006, vol. 78, No. 9, pp. 1231-1232.

(56) References Cited

OTHER PUBLICATIONS

Wang et al., "Nogo-A is associated with secondary degeneration of substatia nigra in hypertensive rats with focal cortical infarction", Brain Research, 2012, vol. 1469, pp. 153-163.

Ward et al., "Docosahexaenoic acid prevents white matter damage after spinal cord injury", Journal of Neurotrauma, Oct. 2010, vol. 27, pp. 1769-1780.

Xiong et al. "Age-related white matter changes." Journal of aging research 2011 (2011).

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      WT/PAH-enu2 forward primer

<400> SEQUENCE: 1
ccgtcctgtt gctggcttac                                               20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      WT/PAH-enu2 reverse primer

<400> SEQUENCE: 2
caggtgtgta catgggctta gatc                                          24

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      WT probe
<220> FEATURE:
<221> NAME/KEY: modified_base
<222> LOCATION: (8)..(10)
<223> OTHER INFORMATION: n is a, c, g, or t
```

```
-continued

<220> FEATURE:
<221> NAME/KEY: modified_base
<222> LOCATION: (13)..(13)
<223> OTHER INFORMATION: n is a, c, g, or t

<400> SEQUENCE: 3
ccgagtcnnn cantgca                                              17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      PAH-enu2 probe
<220> FEATURE:
<221> NAME/KEY: modified_base
<222> LOCATION: (8)..(10)
<223> OTHER INFORMATION: n is a, c, g, or t

<400> SEQUENCE: 4
ccgagtcnnn cactgca                                              17
```

METHOD FOR IMPROVING RECOGNITION AND/OR WORKING MEMORY IN HYPERPHENYLALANIMENIA AND PHENYLKETONURIA PATIENTS

CROSS-REFERENCE TO RELATED APPLICATIONS

This application is the National Phase of International Patent Application No. PCT/NL2016/050735, filed Oct. 24, 2016, published on Apr. 27, 2017 as WO 2017/069632 A1, which claims priority to International Patent Application No. PCT/NL2015/050740, filed Oct. 23, 2015. The contents of these applications are herein incorporated by reference in their entirety.

SEQUENCE LISTING

The instant application contains a Sequence Listing which has been filed electronically in ASCII format and is hereby incorporated by reference in its entirety. Said ASCII copy, created on Feb. 27, 2020, is named 069818-3670_SL.txt and is 1,566 bytes in size.

The invention is in the field of medical nutrition and more particularly relates to compositions for use in improving conditions associated with phenylketonuria (PKU) and hyperphenylalanimenia. In a preferred aspect, the invention pertains to improving recognition and/or working memory in patients suffering from PKU or hyperphenylalanimenia.

BACKGROUND

Phenylalanine is an essential amino acid, therefore it must be provided for in the diet, as it is vital for protein synthesis and normal growth and development. The first step in the metabolism of phenylalanine is the conversion of phenylalanine to tyrosine, a reaction catalyzed by phenylalanine hydroxylase that predominantly occurs within the liver. Tyrosine is then converted to the thyroid hormone thyroxine, the neurotransmitter dopamine, the adrenal hormones adrenaline and nor-adrenaline and the pigment melanin.

The genetic mutations characteristic for Phenylketonuria (PKU) impair the proper functioning of the enzyme phenylalanine hydroxylase, who are therefore unable to metabolize phenylalanine to tyrosine, and therefore phenylalanine accumulates within the body. Accumulated phenylalanine is converted by other pathways to various metabolites including phenyl pyruvic acid and phenyl acetic acid. These pathways and metabolites are found within healthy individuals, however in the PKU patient the absence of PAH results in these pathways occurring more frequently leading to abnormally high levels of the metabolites they generate. Increased concentrations of phenylalanine and its metabolites causes the disruption and inhibition of various biochemical processes, which is thought to lead to the clinical manifestations as seen in PKU.

SUMMARY OF THE INVENTION

The inventors realized that in PKU patients recognition and/or working memory can be improved using a nutritional therapy aiming at reducing phenylalanine levels in the brain in combination with specific actives stimulating recognition and/or working memory. In contrast to neurodegenerative disorders, increases in phenylalanine in PKU and hyperphenylalanimenia are inherited diseases that develop from birth resulting in decreased cerebral protein synthesis thereby potentially impairing the formation of synapses in the neuronal network of the brain. The mechanism underlying the neurological problems in Alzheimer's and dementia is therefore very different from the underlying mechanisms in PKU and hyperphenylalanimenia.

The method, combination and composition of the invention comprises therapeutic amounts of: (i) at least one ω-3 polyunsaturated fatty acid (LCPUFA) selected from the group consisting of docosahexaenoic acid (DHA), eicosapentaenoic acid (EPA) and docosapentaenoic acid (DPA); (ii) choline, a choline salt and/or choline ester; and (iii) at least one, more preferably at least two B vitamins selected from the group consisting of vitamin B6, vitamin B12 and vitamin B9, including functional equivalents thereof, preferably vitamin B6 and/or vitamin B12, and functional equivalents thereof.

The method, combination or composition may further comprise therapeutically effective amounts of said one of more of uridine, cytidine and/or an equivalent thereof, including salts, phosphates, acyl derivatives and/or esters. The method, combination or composition of the invention preferably comprises therapeutic amounts of said at least one, preferably both, of vitamin D and vitamin K, including their equivalents.

LIST OF PREFERRED EMBODIMENTS

1. Use of a composition in the manufacture of a product for therapeutically improving, promoting, restoring or maintaining recognition and/or working memory in a subject suffering from PKU and/or in a subject suffering from or at increased risk of impaired recognition and/or working memory associated with PKU, said composition comprising therapeutic amounts of: (i) at least one ω-3 polyunsaturated fatty acid (LCPUFA) selected from the group consisting of docosahexaenoic acid (DHA), eicosapentaenoic acid (EPA) and docosapentaenoic acid (DPA); (ii) choline, a choline salt and/or choline ester; and (iii) at least one B vitamin selected from the group consisting of vitamin B6, vitamin B12 and vitamin B9, including functional equivalents thereof, preferably vitamin B6 and/or vitamin B12, and functional equivalents thereof
2. Use according to embodiment 1, wherein the composition further comprises therapeutically effective amounts of one of more of uridine, cytidine and/or an equivalent thereof, including salts, phosphates, acyl derivatives and/or esters.
3. Use according to embodiment 1 or 2, wherein the composition further comprises therapeutic amounts of vitamin D and/or vitamin K, and functional equivalents thereof
4. Use according to any one of the preceding embodiments, wherein the composition further comprises therapeutic amounts of at least one, preferably at least two, most preferably all of the antioxidants selected from the group consisting of selenium, vitamin C and vitamin E, and functional equivalents thereof, preferably comprising at least selenium.
5. Use according to any of the preceding embodiments, wherein the composition comprises proteinaceous matter which is essentially free of phenylalanine, and wherein the sum of threonine, valine, histidine and methionine is at least 12 wt %, preferably at least 13 wt %, more preferably at least 14 wt %, even more preferably 15-60 wt %, most preferably 16-40 wt % based on total proteinaceous matter and/or wherein the composition comprises leucine in free form, wherein the total amount of L-leucine provided by the proteinaceous matter amounts to at least 7 wt %, preferably at least 8 wt %, more preferably at least 9-20 wt %, based on total proteinaceous matter.

6. A composition for use in therapeutically improving, promoting, restoring or maintaining recognition and/or working memory in a subject suffering from PKU and/or in a subject suffering from or at increased risk of impaired recognition and/or working memory associated with PKU, said composition comprising therapeutic amounts of: (i) at least one ω-3 polyunsaturated fatty acid (LCPUFA) selected from the group consisting of docosahexaenoic acid (DHA), eicosapentaenoic acid (EPA) and docosapentaenoic acid (DPA); (ii) choline, a choline salt and/or choline ester; and (iii) at least one B vitamin selected from the group consisting of vitamin B6, vitamin B12 and vitamin B9, including functional equivalents thereof, preferably vitamin B6 and/or vitamin B12, and functional equivalents thereof 7. A combination of therapeutic amounts of: (i) at least one ω-3 polyunsaturated fatty acid (LCPUFA) selected from the group consisting of docosahexaenoic acid (DHA), eicosapentaenoic acid (EPA) and docosapentaenoic acid (DPA); (ii) choline, a choline salt and/or choline ester; and (iii) at least one B vitamin selected from the group consisting of vitamin B6, vitamin B12 and vitamin B9, including functional equivalents thereof, preferably vitamin B6 and/or vitamin B12, and functional equivalents thereof, for use in therapeutically improving, promoting, restoring or maintaining recognition and/or working memory in a subject suffering from PKU and/or in a subject suffering from or at increased risk of impaired recognition and/or working memory associated with PKU.

8. A method for therapeutically improving, promoting, restoring or maintaining recognition and/or working memory in a subject suffering from PKU and/or in a subject suffering from or at increased risk of impaired recognition and/or working memory associated with PKU, said method comprising administering to said subject a composition comprising therapeutic amounts of: (i) at least one ω-3 polyunsaturated fatty acid (LCPUFA) selected from the group consisting of docosahexaenoic acid (DHA), eicosapentaenoic acid (EPA) and docosapentaenoic acid (DPA); (ii) choline, a choline salt and/or choline ester; and (iii) at least one B vitamin selected from the group consisting of vitamin B6, vitamin B12 and vitamin B9, including functional equivalents thereof, preferably vitamin B6 and/or vitamin B12, and functional equivalents thereof.

9. A composition suitable for PKU patients, comprising therapeutic amounts of: (i) at least one ω-3 polyunsaturated fatty acid (LCPUFA) selected from the group consisting of docosahexaenoic acid (DHA), eicosapentaenoic acid (EPA) and docosapentaenoic acid (DPA); (ii) choline, a choline salt and/or choline ester; and (iii) at least one B vitamin selected from the group consisting of vitamin B6, vitamin B12 and vitamin B9, including functional equivalents thereof, preferably vitamin B6 and/or vitamin B12, and functional equivalents thereof, and at least one of vitamin D and vitamin K, including functional equivalents thereof.

10. The composition according to embodiment 9, further comprising therapeutically effective amounts of said one of more of uridine, cytidine and/or an equivalent thereof, including salts, phosphates, acyl derivatives and/or esters.

11. The composition according to embodiment 9 or 10, further comprising proteinaceous matter which is essentially free of phenylalanine, and wherein the sum of threonine, valine, histidine and methionine is at least 12 wt %, preferably at least 13 wt %, more preferably at least 14 wt %, even more preferably 15-60 wt %, most preferably 16-40 wt % based on total proteinaceous matter and/or wherein the composition comprises leucine in free form, wherein the total amount of L-leucine provided by the proteinaceous matter amounts to at least 7 wt %, preferably at least 8 wt %, more preferably at least 9-20 wt %, based on total proteinaceous matter.

DETAILED DESCRIPTION OF THE INVENTION

Figure 1A:
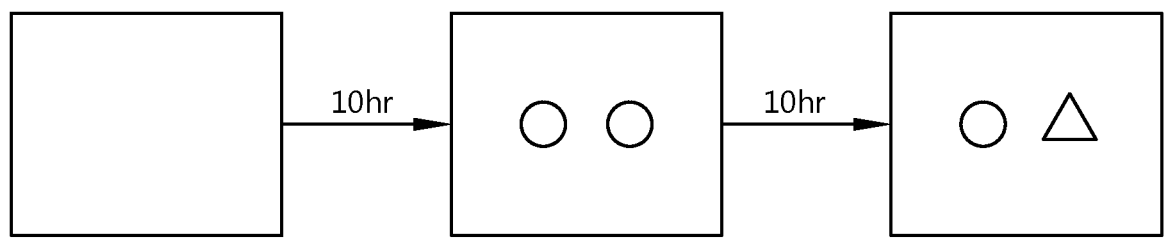
FIG. 1A—schematic representation of novel object recognition setup.

In one aspect, the invention pertains to the use of a composition in the manufacture of a product for therapeutically improving, promoting, restoring or maintaining recognition and/or working memory in a subject suffering from PKU and/or in a subject suffering from or at increased risk of impaired recognition and/or working memory associated with PKU. The invention also pertains to a composition, combination or product for use in for therapeutically improving, promoting, restoring or maintaining recognition and/or working memory in a subject as defined here above. The invention also relates to a method for improving, promoting, restoring or maintaining recognition and/or working memory in a subject as defined here above, said method comprising administering a composition, combination or product to a subject suffering from PKU and/or a subject suffering from or at increased risk of impaired recognition and/or working memory associated with PKU. The invention is particularly directed to recognition memory, specifically novel object and spatial object recognition memory.

In another aspect, the invention pertains to the use of a composition in the manufacture of a product for treating a subject suffering from PKU. The invention also pertains to a composition, combination or product for use in treating a subject suffering from PKU. The invention also relates to a method for treating a subject suffering from PKU, said method comprising administering a composition, combination or product to said subject. In one embodiment, the 'treatment' is directed to prevent recognition and/or working memory deficits associated with PKU. Associated therewith, treatment may involve the improvement, promotion, restoration or maintenance of recognition and/or working memory in PKU patients. The invention is particularly directed to recognition memory, specifically novel object and spatial object recognition memory.

In the context of the present invention, the term 'recognition' and the term 'recognition memory' are synonymous, and refer to a subcategory of declarative memory. Preferably, both terms refer to the ability to recognize previously encountered events, objects, or people; and when the previously-experienced event, person, or thing is re-experienced, this environmental content is matched to stored memory representations, eliciting matching signals. Recognition can be regarded as involving both recollection (also referred to as remembering, regarded as a slow, controlled search process) and familiarity (also referred to as knowing, and considered as a fast, automatic process). Recognition (memory) is not confined to the visual domain, and can involve each of the five traditional sensory modalities (i.e. sight, hearing, touch, smell, and taste). Although most neuroscientific research has focused on visual recognition, there have also been studies (known in the art) related to audition (hearing), olfaction (smell), gustation (taste), and tactition (touch). The methods, combinations and compositions according to the invention are preferably directed to improving audition (or hearing, or verbal) recognition, and/or visual recognition, and more preferably to improving both verbal and visual recognition. The invention particularly deals with novel object and spatial object recognition memory, and well-defined tests are available in the art, typically with delay trial intervals of at least 1 min, 1 hour, 3 hours, 5 hours and/or 10 hours. The evidence provided here is in accordance therewith.

In the context of the present invention, the term 'working memory' is understood the system responsible for the transient holding and processing of new and already-stored information, and is an important process for reasoning, comprehension, and memory updating. Working memory is a theoretical framework that refers to structures and processes used for temporarily storing and manipulating information.

In the above cases, the subject is preferably a human subject. The human subject suffering from PKU or hyperphenylalanimenia can be an infant or child up to 18 years of age, or an adult between 18 and 50 years of age. In one embodiment of the invention, the method for preserving and improving cognitive function and reducing cognitive deficit in phenylketonuria or hyperphenylalanimenia patients and/or preserving and improving cognitive function and reducing cognitive deficit associated with phenylketonuria or hyperphenylalanimenia, particularly learning and memory, are excluded from the invention.

The composition, method and combination will be outlined in more detail here below.

Firstly, should the composition, method and combination of the invention involve the administration of proteinaceous matter, it should be 'substantially devoid from Phe' or 'essentially free of phenylalanine', meaning that less than 2 wt % phenylalanine, more preferably less than 1 wt % Phe, more preferably less than 0.5 wt % Phe, even more preferably less than 0.1 wt % Phe, most preferably less than 0.05 wt % Phe, based on the total proteinaceous content of the composition or combination, is present. In order to achieve such low Phe levels, a product according to the invention comprises proteinaceous matter comprising free amino acids (other than phenylalanine) and/or a non-allergenic protein source such as glycomacropeptide (GMP). According to the present invention, 'free amino acids' are amino acids not coupled to other amino acids, but the term includes amino acids salts or di- and tripeptides such as cystine or gly-gly dipeptides. An absolute phenylalanine-free product can be obtained when using free amino acids, and the composition of the amino acids can be easily adapted to the nutritional requirements depending on the age of the patients. Such proteinaceous compositions tailored to PKU patients are available in the art. GMP is a protein originating from casein and is low in phenylalanine, and can improve the taste significantly without significantly increasing the phenylalanine content of the composition or combination. If the composition or combination comprises a protein fraction, it is preferred to involve a mixture of GMP supplemented with free amino acids to the extent desired and/or according to nutritional requirements. The composition or combination preferably comprises at least 50 wt %, preferably 70-90 wt % GMP based on the total protein content, preferably supplemented to 100% with free amino acids.

A preferred amino acid composition according to the present invention has a relatively high content of branched chain amino acids (BCAA) leucine, isoleucine and valine. These amino acids can potentially block the transport of phenylalanine over the intestinal barrier and also over the blood-brain barrier thereby helping in lowering the levels of phenylalanine in the brain, but without wishing to be tied down to any theory, the inventors also believe that adding these amino acids would increase cerebral protein synthesis. The protein fraction preferably comprises at least 15 wt % of these branched chain amino acids (BCAA), more preferably between 15 and 35 wt %, even more preferably between 16 and 30 wt %, particularly 17-25 wt %, most preferably at least 18 wt % based on the total protein content.

The method, composition or combination of the invention preferably comprises L-leucine in free form, wherein the total amount of L-leucine provided by the proteinaceous matter amounts to at least 7 wt %, preferably at least 8 wt %, more preferably 9-20 wt %, most preferably 9-15 wt %, based on total proteinaceous matter. In the context of the invention, the terms 'leucine' and 'L-leucine' are used interchangeably.

In order to improve LAT1-mediated blood-brain barrier transport of large neutral amino acids (LNAAs), it is preferred that the sum of threonine, valine, histidine and methionine at least 12 wt %, preferably at least 13 wt %, more preferably at least 14 wt %, even more preferably 15-60 wt %, most preferably 16-40 wt % based on total proteinaceous matter (i.e. the sum of all amino acids, peptides and proteins and hydrolysates thereof).

In one embodiment, the method, composition or combination of the invention may comprise inositol and/or iodine, preferably at least inositol The method, composition or combination of the invention may comprise Fe minerals.

In the compositions, methods and combinations in accordance with the invention, at least 2, preferably at least 3 of the following ingredients are present, in therapeutically effective amounts.

Vitamin D, Vitamin K

The method, composition or combination of the invention preferably comprises at least one of vitamins K and vitamin D and/or their functional equivalents, preferably both in therapeutically effective amounts. Within the context of the present invention, 'vitamin D' is understood to encompass vitamin $D_2$ (ergocalciferol), vitamin $D_3$ (cholecalciferol). Vitamin D, or a functional equivalent thereof, is preferably present in the method, composition or combination of the invention in an amount to provide a daily dosage in the range of 1 to 100 in particular in the range of 1 to 50 preferably 2-25 preferably at least 3 more preferably at least 4 even more preferably at least 5 more in particular in the range of 5 to 25 even more preferably at least 5-15 μg. In one embodiment, vitamin D, or a functional equivalent thereof, is present in an amount in the range of 1 to 100 in particular in the range of 2 to 50 preferably 2-25 preferably at least 3 more preferably at least 4 even more preferably at least 5 more in particular in the range of 5 to 25 even more preferably at least 5-15 μg per 100 ml of the (liquid) product.

In the context of the invention, 1 IU of vitamin D is the biological equivalent of 0.025 µg. Hence, 1,000 IU is the biological equivalent of 25 µg.

The method, combination or composition according to the invention comprises at least a therapeutically effective amount of vitamin K, including vitamin K1 and/or vitamin K2. Vitamin K2, also known as "menatetrenone", "menaquinone-7", "menaquinone" or "menadione", is a group name for a family of related compounds, generally subdivided into short-chain menaquinones, with menatetrenone ("MK-4") as the most important member, and long-chain menaquinones, of which MK-7, MK-8 and MK-9 are nutritionally the most recognized. Within the context of the present invention, 'vitamin K, or a functional equivalent thereof' is understood to refer to vitamin K1, vitamin K2, menaquinone-4 (MK-4), menaquinone-7 (MK-7). It is preferred that in the composition, Vitamin K, or a functional equivalent thereof, is present in an amount to provide a daily dosage in the range of 1 to 100 in particular in the range of 5 to 50 more in particular at least 7 preferably at least 8 more preferably at least 9 even more preferably in the range of 10 to 50 particularly at least 11, 12, 13, 14, 15 preferably up to 40 more preferably up to 30 µg. In one embodiment, vitamin K, or a functional equivalent thereof, is present in an amount in the range 1 to 100 in particular in the range of 5 to 50 more in particular at least 7 preferably at least 8 more preferably at least 9 even more preferably in the range of 10 to 50 particularly at least 11, 12, 13, 14, 15 preferably up to more preferably up to 30 µg per 100 ml of the (liquid) product. Preferably vitamin K is present as vitamin K1.

DHA/EPA/DPA

The composition or combination of the invention preferably comprises at least one ω-3 long-chain polyunsaturated fatty acid (LC PUFA; having a chain length of 18 and more carbon atoms) selected from the group consisting of docosahexaenoic acid (22:6; DHA), eicosapentaenoic acid (20:5; EPA) and docosapentaenoic acid (22:5 ω-3; DPA), preferably at least one of DHA and EPA. Preferably the present composition or combination contains at least DHA, more preferably DHA and EPA. EPA is converted to DPA (ω-3), increasing subsequent conversion of DPA to DHA in the brain. Hence, the present composition or combination preferably also contains a significant amount of EPA, so to further stimulate in vivo DHA formation.

The LCPUFAs (DHA, EPA and/or DPA) are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition or combination comprises at least DHA in triglyceride form. Suitable ω-3 LCPUFA and/or DHA sources include tuna oil, (other) fish oils, DHA-rich alkyl esters, algae oil, egg yolk, or phospholipids enriched with ω-3 LCPUFA e.g. phosphatidylserine-DHA. Preferably, a composition or combination according to the invention comprises fish oil providing the omega-3 LCPUFA(s), Another particularly suitable source for the omega-3 LCPUFA(s) is algae oil.

If EPA, DHA and/or EPA are present, the total daily dosage of DHA+EPA+DPA taken together is in the range of 0.25 to 5 g per day, more preferably 0.5 to 5 g per day, most preferably 1 to 2.5 g per day. In a preferred embodiment, these amounts are based on the total sum of DHA and EPA if present. DHA is preferably administered in an amount of at least 0.5 g per day, more preferably 0.5 to 2.5 g per day, most preferably at least 1 g per day.

In terms of the composition, combination or method, the proportion of ω-3 LCPUFA (more preferably DHA+EPA+DPA, most preferably DHA+EPA) of the total fatty acids in the composition is preferably 5 to 95 wt %, more preferably 10 to 80 wt %, most preferably 15 to 70 wt %, even more preferably 20 to 60 wt % of the total fatty acids. The present composition or combination preferably comprises 5 to 95 wt % DHA based on total fatty acids, preferably 10 to 75 wt % DHA based on total fatty acids, more preferably 10 to 60 wt %, even more preferably 10-50 wt %, more preferably 10-40 wt %, especially at least 20 wt % DHA, based on total fatty acids of the composition or combination. The present composition or combination preferably comprises 5 to 95 wt % EPA based on total fatty acids, preferably 5 to 75 wt % EPA, even more preferably 5-50 wt %, more preferably 5-25 wt %, most preferably 5-15 wt %, based on total fatty acids of the composition or combination. In terms of DHA content in a composition or combination in accordance with the present invention, the DHA content is preferably 0.5-1.5 g per 100 ml of the (liquid) product. The amount of EPA is preferably at least 0.1 g, more preferably at least 0.2 g of the product. The above-mentioned amounts take into account and optimize several aspects, including taste (e.g. too high LCP levels reduce taste, resulting in a reduced compliance).

In the method, combination or composition of the invention, the ratio of the weight of DHA to EPA is preferably larger than 1, more preferably 2:1 to 10:1, more preferably 2:1 to 5:1. The ratios take into account and optimize the balance between DHA and precursors thereof to ensure optimal effectiveness while maintaining low-volume formulations.

If arachidonic acid (AA) is present or administered, it concerns a very low amount of AA, expressed in terms of a DHA/AA weight ratio in the present composition, combination or method of at least 5, preferably at least 10, more preferably at least 15, preferably at least 20, most preferably at least 25. If AA is administered, it preferably amounts to less than 5 wt. %, more preferably less than 2.5 wt. %, preferably less than 1 wt % based on total fatty acids of the composition or combination.

Uridine, UMP

The method, combination and composition according to the invention preferably comprise one of more of uridine, cytidine and/or an equivalent thereof, including salts, phosphates, acyl derivatives and/or esters. The method, combination and composition preferably comprises at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. In one embodiment, cytidine, CMP, citicoline (CDP-choline) may also be applied in addition to or instead of uridine (equivalent). Preferably, the composition or combination to be administered according to the present invention comprises a source of uridine selected from the group consisting of uridine, deoxyuridine, uridine phosphates, uracil, and acylated uridine.

Preferably, the method, combination and composition according to the invention comprise an uridine phosphate selected from the group consisting of uridine monophosphate (UMP), uridine diphosphate (UDP) and uridine triphosphate (UTP); and/or a cytidine phosphate (CMP, CDP, CTP, preferably CMP). In a preferred embodiment, the composition or combination comprises at least one of the aforementioned uridine phosphates. Most preferably the present composition or combination comprises UMP, as UMP is most efficiently being taken up by the body. Hence, inclusion of UMP in the present method, combination and composition enables a high effectivity or efficacy at the lowest dosage and/or the administration of a low volume to the subject. Preferably at least 50 weight % of the uridine in the present method, combination and composition is provided by UMP, more preferably at least 75 weight %, most preferably at least 95 weight %. Doses administered are given as UMP. The amount of uracil sources can be calculated taking the molar equivalent to the UMP amount (molecular weight 324 Dalton).

The present method preferably comprises the administration of uridine (the cumulative amount of uridine, deoxyuridine, uridine phosphates, nucleobase uracil and acylated uridine derivatives) in an amount of in an amount of 0.05-5 g per day, preferably 0.1-2.5 g per day, more preferably 0.25-1 g per day. The present method preferably comprises the administration of a composition or combination comprising uridine in an amount of 0.05-5 g UMP per 100 ml liquid product, preferably 0.1-2.5 g UMP per 100 ml liquid product, more preferably 0.25-1 g per 100 ml liquid product. The terms product, composition and combination are used interchangeably. Preferably 1-40 mg UMP per kilogram body weight is administered per day, more preferably 5-35, even more preferably 5-30 mg UMP/kg body weight. The above amounts also account for any amounts of cytidine, cytidine phosphates and citicoline incorporated in the composition, combination or method.

Choline

In a preferred embodiment, the method, combination and composition according to the present invention comprise choline, a choline salt and/or choline ester. Herein, the term 'choline' shall be considered to encompass all these equivalents. The choline salt is preferably selected from choline chloride, choline bitartrate, or choline stearate. The choline ester is preferably selected from the group consisting of phosphatidylcholine and lyso-phosphatidylcholine. The present method preferably comprises the administration of more than 0.05 g choline per day, preferably 0.1 to 2 g choline per day, more preferably 0.2 to 1 g choline per day, most preferably 0.2 to 0.5 g choline per day. The present composition or combination preferably comprises 0.05 to 2 g choline per 100 ml of the liquid product, preferably 0.2 to 1 g, more preferably up to 0.5 g choline per 100 ml. The above numbers are based on choline, the amounts of choline equivalents or sources can be calculated taking the molar equivalent to choline into account, based on the molar mass of 104 g choline/mol.

Phospholipids

Preferably, the method, composition and combination according to the present invention comprises phospholipids, preferably 0.1-50 wt % phospholipids based on total weight of lipids, more preferably 0.5-20 wt %, more preferably between 1 and 10% wt. %, most preferably between 1 and 5 wt % based on total weight of lipids. The present method preferably comprises the administration of 50-1000 mg phospholipids. The total amount of lipids is preferably between 10 and 30 wt % on dry matter, and/or between 2 and 10 g lipid per 100 ml for a liquid product. The composition or combination preferably comprises between 0.01 and 1 gram lecithin per 100 ml, more preferably between 0.05 and 0.5 gram lecithin per 100 ml. A composition with these preferred amounts was found to be very effective. In one embodiment, the amount of phospholipids is between 0.01 and 0.5 g, more preferably between 0.05 and 0.25 g per 100 ml.

B Vitamins

The method, combination and composition according to the present invention preferably comprise at least one B complex vitamin. The vitamin B is selected from the group of vitamin B1 (thiamine), vitamin B2 (riboflavin), vitamin B3 (niacin or niacinamide), vitamin B5 (panthothenic acid), vitamin B6 (pyridoxine, pyridoxal, or pyridoxamine, or pyridoxine hydrochloride), vitamin B7 (biotin), vitamin B9 (folic acid or folate), and vitamin B12 (various cobalamins). Functional equivalents are encompassed within these terms.

Preferably at least one, more preferably at least two B vitamins are selected from the group consisting of vitamin B6, vitamin B12 and vitamin B9, including their functional equivalents, preferably vitamins B6 and/or B12. Again, functional equivalents are encompassed within these terms.

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (TOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose preferably does not exceed the tolerable upper intake levels (UL), as recommended by IOM.

If present or administered, the vitamin B6 is preferably present in an amount to provide a daily dosage in the range of 0.1 to 50 mg, in particular in the range of 0.5 to 10 mg, more in particular in the range of 0.5 to 5 mg. The present composition or combination preferably comprises 0.1 to 50 mg vitamin B6 per 100 ml (liquid) product, more preferably 0.5 to 10 mg vitamin B6 per 100 ml (liquid) product, more preferably 0.5 to 5 mg vitamin B6 per 100 ml (liquid) product.

If present or administered, the vitamin B12 is preferably present in an amount to provide a daily dosage in the range of 0.5 to 15 µg, in particular in the range of 1 to 10 µg, more in particular in the range of 1 to 5 µg. The present composition or combination preferably comprises 0.5-15 µg vitamin B12 per 100 ml (liquid) product, more preferably 1 to 10 µg vitamin B12 per 100 ml (liquid) product, more preferably 1 to 5 µg vitamin B12 per 100 ml (liquid) product. The term "vitamin B12" incorporates all cobalamin equivalents known in the art.

Throughout the application, the terms 'folic acid', 'folate' and 'B9' are used interchangeably. If present or administered, the vitamin B9 is preferably present in an amount to provide a daily dosage in the range of 0.05 to 1 mg, in particular in the range of 0.05 to 0.5 mg, preferably up to 0.4 mg, more preferably up to 0.3 mg, even more in particular in the range of 0.05 to 0.2 mg, preferably below 0.19 mg, below 0.18 mg, below 0.17 mg, below 0.16 mg, particularly 0.05-0.15 mg, most preferably up to 0.1 mg per day. The present composition or combination preferably comprises 0.05 to 1 mg folic acid per 100 g (liquid) product, more preferably 0.05 to 0.5 mg folic acid per 100 ml (liquid) product, preferably up to 0.4 mg, more preferably up to 0.3 mg, even more preferably 0.05 to 0.2 mg folic acid per 100 ml (liquid) product, preferably below 0.19 mg, below 0.18 mg, below 0.17 mg, below 0.16 mg, most preferably 0.05-0.15 mg, most preferably up to 0.1 mg folic acid per 100 ml product. Folates include folic acid, folinic acid, methylated, methenylated and formylated forms of folates, their salts or esters, as well as their derivatives with one or more glutamic acid, and all in either reduced or oxidized form.

If B vitamins are present, it is preferably vitamins B6 and/or B12.

Vitamins C, E, Selenium

The method, combination and composition of the invention preferably involves at least one, preferably at least two, most preferably all of the antioxidants selected from the group consisting of selenium, vitamin C and vitamin E, and functional equivalents thereof. Selenium is the most preferred antioxidant.

Vitamin C, or a functional equivalent thereof, may be present or administered in an amount to provide a daily dosage in the range of 0.01 to 2 g, in particular in the range of 0.025 to 0.5 g, more in particular in the range of 0.04 to 0.15 g. In one embodiment, vitamin C, or a functional equivalent thereof, is given in an amount in the range of 0.025 to 2 g, in particular in the range of 0.04 to 0.5 g, more in particular in the range of 0.04 to 0.15 g per 100 ml of the (liquid) product.

Tocopherol and/or an equivalent thereof (i.e. a compound having vitamin E activity) may be present in an amount to provide a daily dosage in the range of 0.01 to 0.5 g, in particular in the range of 0.01 to 0.25 g, more in particular in the range of 0.025 to 0.1 g, particularly 0.025 to 0.05 g, to prevent oxidative damage resulting from dietary PUFA. In one embodiment, tocopherol and/or equivalent is present in an amount in the range of 0.01 to 0.5 g, in particular in the range of 0.01 to 0.25 g, more in particular in the range of 0.02 to 0.1 g, particularly 0.025 to 0.05 g per 100 ml of the product. The term "tocopherol and/or an equivalent thereof", and 'alpha-TE', as used in this description, comprises tocopherols, tocotrienols, pharmaceutical and/or nutritional acceptable derivatives thereof and any combination thereof. The above numbers correspond to the amount of alpha-tocopherol, recognized in the art.

The present composition preferably contains selenium, because of its excellent antioxidant activity. The present method preferably provides the administration of a composition or a combination comprising between 0.01 and 5 mg selenium per 100 ml liquid product, preferably between 0.025 and 0.1 mg selenium per 100 ml liquid product. The amount of selenium administered per day is preferably more than 0.01 mg, more preferably 0.01 to 0.5 mg, most preferably at least 0.025 mg per day.

In a preferred embodiment, the method, combination or composition of the invention preferably comprises therapeutic amounts of: (i) said at least one ω-3 polyunsaturated fatty acid (LCPUFA) selected from the group consisting of docosahexaenoic acid (DHA), eicosapentaenoic acid (EPA) and docosapentaenoic acid (DPA); (ii) said choline, a choline salt and/or choline ester; and (iii) said at least one, more preferably at least two B vitamins selected from the group consisting of vitamin B6, vitamin B12 and vitamin B9, including functional equivalents thereof, preferably vitamin B6 and/or vitamin B12, and functional equivalents thereof.

The method, combination or composition may further comprise therapeutically effective amounts of said one of more of uridine, cytidine and/or an equivalent thereof, including salts, phosphates, acyl derivatives and/or esters. The method, combination or composition of the invention preferably comprises therapeutic amounts of said at least one, preferably both, of vitamin D and vitamin K, including their equivalents. These components and preferred amounts are outlined here above.

With the above restraints, the embodiments of the invention preferably pertain to a method, composition or combination as defined here above, comprising administering, per daily dosage or per 100 ml product, at least 3, 4, 5, 6, 7, 8, 9 or all of:

0.25 to 5 g, preferably 0.5 to 5 g, more preferably 1 to 2.5 g of DHA+EPA+DPA taken together;

0.05-5 g, preferably 0.1-2.5 g, more preferably 0.25-1 g of uridine;

0.1 to 2 g, preferably 0.2 to 1 g, more preferably 0.2 to 0.5 g choline;

0.05-0.6 g, preferably 0.05-0.6 g, more preferably 0.06-0.2 g phospholipids;

0.1 to 50 mg, preferably 0.5 to 10 mg, more preferably 0.5 to 5 mg of vitamin B6;

0.5 to 15 µg, preferably 1 to 10 µg, more preferably 1 to 5 µg of vitamin B12;

0.05 to 0.5 mg, preferably 0.05 to 0.2 mg, preferably less than 0.19 mg, more preferably less than 0.18 mg, preferably less than 0.17 mg, more preferably less than 0.16 mg, more preferably 0.05 to 0.15 mg vitamin B9;

0.01 to 2 g, preferably 0.025 to 0.5 g, more preferably 0.04 to 0.15 g of Vitamin C;

0.01 to 0.5 g, preferably 0.015 to 0.25 g, more preferably 0.02 to 0.1 g of alpha-tocopherol; and more than 0.01 mg, preferably 0.01 to 0.5 mg, more preferably at least 0.025 mg selenium.

The method, composition or combination may further comprise, per daily dosage or per 100 ml product:

1 to 100 µg, in particular in the range of 1 to 50 µg, preferably 2-25 µg, preferably at least 3 µg, more preferably at least 4 µg, even more preferably at least 5 µg, more in particular in the range of 5 to 25 µg, even more preferably at least 5-15 µg of vitamin D; and/or 1 to 100 µg, preferably 5 to 50 µg, preferably at least 7 µg, preferably at least 8 µg, more preferably at least 9 µg, even more preferably in the range of 10 to 50 µg, particularly at least 11, 12, 13, 14, 15 preferably up to 40 more preferably up to 30 µg of Vitamin K, preferably vitamin K1.

It is preferred that both vitamin D and vitamin K are present.

Preferably L-leucine is also present in the aforementioned amounts and/or the sum of threonine, valine, histidine and methionine is preferably at least 14 wt %, preferably at least 15-60 wt %, more preferably 16-40 wt %, based on total proteinaceous matter.

More preferably, the composition comprises, per daily dose or preferably per 100 ml composition:

0.1-0.5 g, preferably 0.2-0.4 g EPA, 0.5-1.5 g, preferably 0.75-1 g DHA, 0.1-0.5 g, preferably 0.2-0.4 g choline, 0.05-0.5 g, preferably 0.06-0.2 g phospholipids, 0.25-0.8 g, preferably 0.4-0.7 g UMP (uridine monophosphate), 0.01-0.05 g, preferably 0.015-0.04 g vitamin E (alpha-TE), 0.04-0.1 g, preferably 0.04-0.09 g vitamin C, 0.035-0.08 mg, preferably 0.035-0.07 mg selenium, 1-5 preferably 2-4 µg vitamin B12, 0.5-3 mg, preferably 0.5-2 mg vitamin B6, and 0.05-0.2 mg, preferably less than 0.19 mg, more preferably less than 0.18 mg, preferably less than 0.17 mg, more preferably less than 0.16 mg, preferably 0.05-0.15 mg, more preferably 0.05-0.1 mg folic acid.

The composition may further comprise vitamin D and/or vitamin K in the aforementioned amounts. Preferably L-leucine is also present in the aforementioned amounts and/or the sum of threonine, valine, histidine and methionine is preferably at least 12 wt %, preferably at least 13 wt %, more preferably at least 14 wt %, even more preferably 15-60 wt %, more preferably 16-40 wt %, based on total proteinaceous matter.

In one aspect of the invention, the compositions either as complete nutrition or as a supplement as detailed above are intended for use in the treatment of phenylketonuria patients.

EXAMPLES

Example 1—Exemplary Composition for Use According to the Invention

|  | invention formula (per serving or per day) |
|---|---|
| Energy (kcal) | 173.5 |
| Protein/Protein Equivalent* (g) | 20 |
| Carbohydrates (g) | 16.5 |
| Fat (g) | 3.05 |
| DHA (22:6n-3; mg) | 0.88 |
| Micronutrients* | |
| Calcium (mg) | 356 |
| Phosphorus (mg) | 276 |
| Vitamin E (mg α-TE) | 33.6 |
| Vitamin C (mg) | 44.4 |
| Vitamin D (μg) | 6 |
| Vitamin K (μg) | 20 |
| Folic acid (μg) | 160 |
| Niacin/Vitamin B3 (mg) | 7.1 |
| Vitamin B6 (mg) | 0.58 |
| Vitamin B12 (μg) | 1.8 |
| Choline (mg) | 153 |
| Nucleotides | |
| Uridine-5'-monophosphate (mg) | 625 |

*The term 'protein equivalent' is an art-recognized term to express the amounts of the free amino acids as the amount of amino acids as if it was part of a protein, i.e. the weight value of amino acids is understood as the protein equivalent weight value, unless otherwise specified. The contribution of the amino acids to protein represents about 81% of the weight of the individual amino acids.

Experimental Evidence: Effect of the Combination According to the Invention on Recognition and Working Memory in a PKU Model Material and Methods Animals & Diets Used in the Experiment SNC is the active supplement that was added to a basal animal chow. The supplement involved a combination of nutrients including uridine-5'-monophosphate, choline, and the omega-3 polyunsaturated fatty acids (LCPUFAs) docosahexaenoic acid (DHA) and eicosapentaenoic acid as it is represented in table 1 here below.

TABLE 1

SNC composition added to mice diet

| component | Amount per 100 gram of mice diet |
|---|---|
| EPA | 200 mg |
| DHA | 3000 mg |
| Phospholipids | 755 mg |
| Choline | 313 mg |
| UMP | 1000 mg |
| Vitamin E (alpha-TE) | 157 mg |
| Vitamin C | 160 mg |
| Selenium | 1.1 μg |
| Vitamin B12 | 1.1 μg |
| Vitamin B6 | 2.7 mg |
| Folic acid | 700 μg |

In this experiment, the BTBR Pah$^{enu2}$ mouse model was used. Male and female homozygous (PKU) mice and wild-type (WT) littermates were obtained from our own breeding. Male and female mice were housed in separate rooms under the same 12:12 light/dark cycle, temperature and humidity conditions. 48 PKU individuals and 48 WT mice were subdivided into four experimental groups, receiving diets with and without SNC. The basal formula for all diets was AIN93G (Research Diet Services, Wijk bij Duurstede).

This resulted in the following four groups:
1. WT control
2. WT+SNC
3. PKU control
4. PKU+SNC The levels of amino acids within the food are depicted in table 2. All diets met the minimal nutritional requirement for laboratory animals. Following weaning at P28, the animals were genotyped and allocated to the different groups. Starting at P31, the animals had ad libitum access to these diets and water for 12 weeks.

All animals were weighed daily between 16:00-18:00 in the first week of the experiment (PND 31-PND 38) and from then on weekly. Food intake was measured daily.

TABLE 2

Amino acid levels in the different nutritional compositions of the treatment groups

|  | g/100 g diet Control diet | g/100 g diet SNC diet |
|---|---|---|
| Alanine | 0.33 | 0.33 |
| Arginine | 0.45 | 0.45 |
| Aspartic acid | 0.80 | 0.80 |
| Cystine | 0.24 | 0.24 |
| Glutamic acid | 2.55 | 2.55 |
| Glycine | 0.23 | 0.23 |
| Histidine | 0.33 | 0.33 |
| Isoleucine | 0.59 | 0.59 |
| Leucine | 1.09 | 1.09 |
| Lysine | 0.92 | 0.92 |
| Methionine | 0.33 | 0.33 |
| Phenylalanine | 0.62 | 0.62 |
| Proline | 1.43 | 1.43 |
| Serine | 0.67 | 0.67 |
| Threonine | 0.47 | 0.47 |
| Tryptophan | 0.16 | 0.16 |
| Tyrosine | 1.50 | 1.50 |
| Valine | 0.70 | 0.70 |

Genotyping

To establish genotype of the animals, quantitative PCR (qPCR) analysis was performed on DNA extracted from tail tissue. The DNA isolation procedure was initiated by incubating tail tissue in 0.5 mL mouse tail lysis buffer (100 mM Tris-HCl, pH 8.5; 5 mM EDTA, pH 8.0; 200 mM NaCl; 0.2% (w/v) SDS) and proteinase K (100 μg/ml, ratio 100:1) overnight at 55° C. at 600 rounds/minute (rpm). The next day the samples were vortexed and centrifuged for 10 min at 13.000 rpm. Subsequently, 450 μL of the supernatant was transferred into a new tube containing 0.5 mL isopropanol. After gently mixing of these solutions, the tube was centrifuged for 10 min at 6000 rpm. The supernatant was removed and the pelleted DNA was air dried for at least 30 min. To prepare the DNA for qPCR, the pelleted DNA was re-suspended in 200 μl TE-buffer (10 mM Tris-HCl; 1 mM EDTA), vortexed, and incubated for 10 min. at 55° C. Subsequently, the samples were centrifuged for 10 min at 15.000 relative centrifugal force (rcf), 50 times diluted with mineralized water, vortexed and again centrifuged for 10 min at 15.000 rcf.

A 96-wells plate (Biorad, HSP-9601) was loaded with 2 μl of the samples together with 5 μL of Mastermix. This mastermix contained:

```
TE-Buffer
PCR-mix (Bioline SensiMixTM Probe Kit
(500 reactions))
WT/PAH-enu2 forward
CCG TCC TGT TGC TGG CTT AC
(SEQ ID NO: 1)
```

```
WT/PAH-enu2 reverse
CAG GTG TGT ACA TGG GCT TAG ATC
(SEQ ID NO: 2)

WT probe
CCG AGT CZZ LCA LTG CA (SEQ ID NO: 3)

PAH-enu2 probe
CCG AGT CZL LCA CTG CA (SEQ ID NO: 4)
```

The primers were based on Genbank and replicated according to guidelines of Eurogentec. The WT probe was tagged with a FAM fluorophore and the PKU probe was tagged with a Yakima Yellow fluorophore (Epoch Biosciences). The plate was run in an ABI Prism 7500 sequence detection system. The cycle parameters were 95° C. for 10 min, 95° C. for 0.15 min and 60° C. for 1 min. This cycle was repeated 39 times.

Novel Object Recognition

Figure 1B:
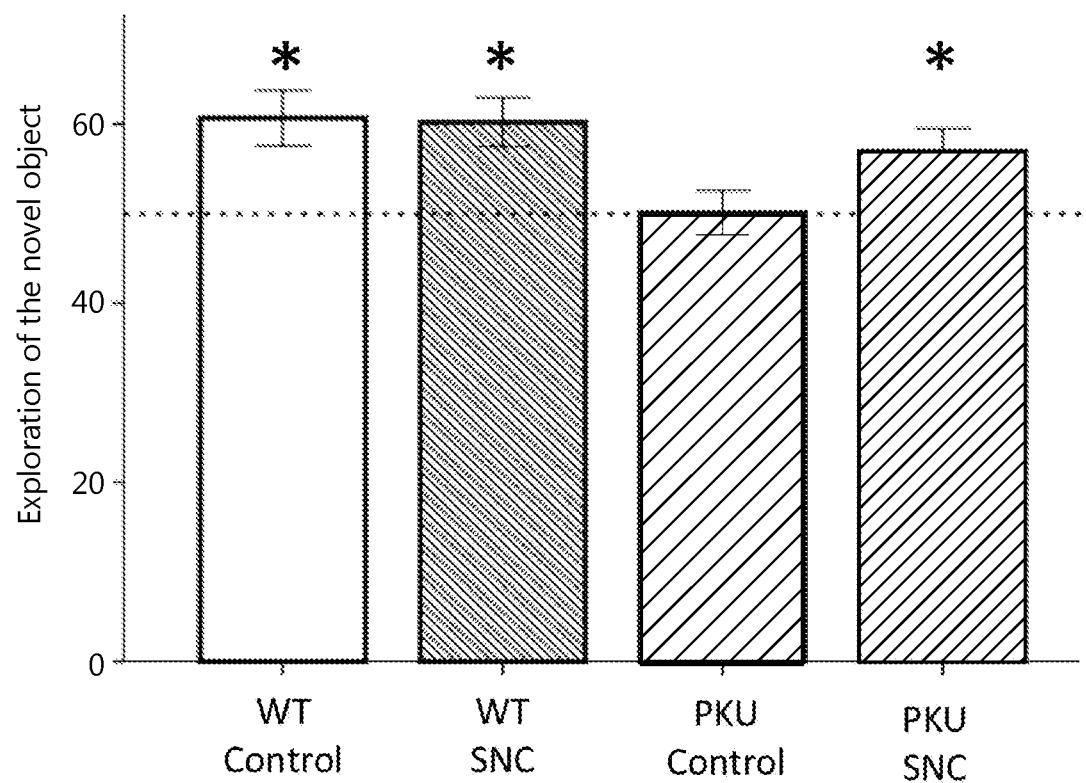
FIG. 1B—Assessing intervention effect in terms of novel objection recognition results in PKU model mice (PKU') and control mice (WV)

In week 16, all animals were subjected to the novel object recognition test (schematic representation in FIG. 1A). Mice were allowed to explore a square open field for 10 minutes. 10 hours later, they were placed in the same open field, but with two similar objects placed in the center of the open field. Another 10 hours later, animals were placed back to explore 2 objects, of which one was a familiar object, whereas the other was novel. The percentage of time to explore the novel vs the familiar object was calculated and is shown in FIG. 1B.

When testing whether the groups performed significantly better than chance using a t-test with Bonferroni correction for multiple testing, both wildtype groups performed significantly better (i.e. explored the novel object more than the familiar object). The PKU control group did not perform better than chance level, suggesting that these mice were impaired in novel object recognition. The PKU animals given the diet containing SNC did perform better than chance, thus indicating that SNC improves novel object recognition in PKU mice.

Spatial Object Recognition

Figure 2A:
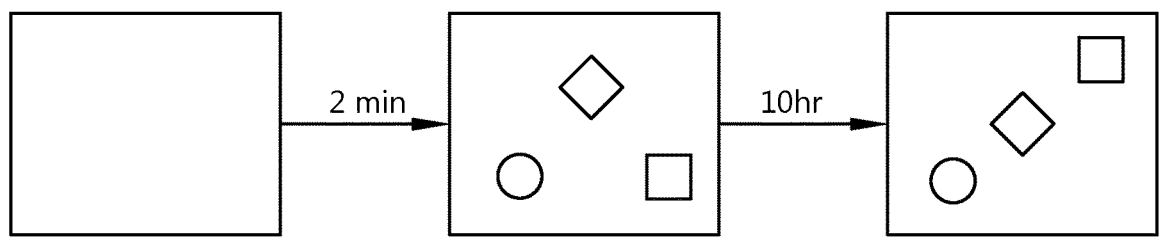
FIG. 2A—schematic representation of novel object recognition setup.
Figure 2B:
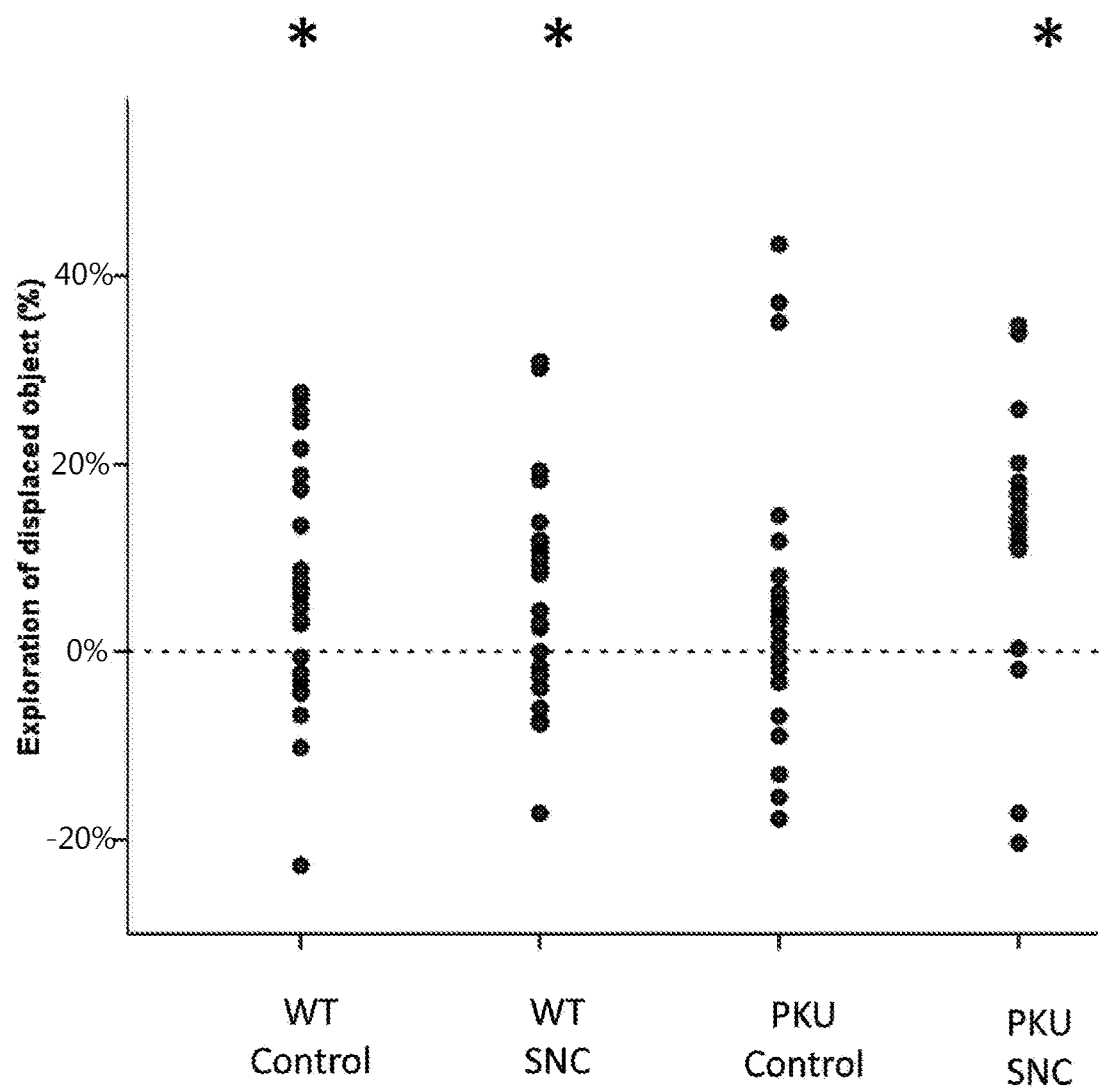
FIG. 2B—Assessing intervention effect in terms of spatial object recognition results in PKU model mice (PKU') and control mice (WV).

In week 16, all animals were subjected to the spatial object recognition test (schematic representation in FIG. 2B). Mice were allowed to explore a square open field for 10 minutes. 2 minutes later, they were placed in the same open field, but with three objects placed in the of the open field. 10 hours later, animals were placed back to explore the objects, of which one displaced. The percentage of time to explore the displaced object was calculated and is shown in FIG. 2B.

Since there was quite some spread in the data, individual data points are shown. When testing whether the groups performed significantly better than chance using a t-test with Bonferroni correction for multiple testing, both wildtype groups performed significantly better (i.e. explored the displaced object more than the other objects). The PKU control group did not perform better than chance level, suggesting that these mice were impaired in spatial object recognition. The PKU animals given the diet containing SNC did perform better than chance, thus indicating that SNC improves spatial object recognition in PKU mice.

The invention claimed is:

1. A method for therapeutically improving, promoting, restoring or maintaining recognition and/or working memory in a subject suffering from phenylketonuria (PKU) or in a subject suffering from or at increased risk of impaired recognition and/or working memory associated with PKU, the method comprising administering to the subject in need thereof a composition comprising therapeutic amounts of:
(i) at least one ω-3 polyunsaturated fatty acid (LCPUFA) selected from the group consisting of docosahexaenoic acid (DHA), eicosapentaenoic acid (EPA) and docosapentaenoic acid (DPA);
(ii) choline, a choline salt and/or choline ester;
(iii) at least one vitamin B selected from the group consisting of vitamin B6, vitamin B12, vitamin B9, and functional equivalents thereof;
(iv) at least one of vitamin D, vitamin K, and functional equivalents thereof; and
(v) proteinaceous matter which is essentially free of phenylalanine, and wherein the sum of threonine, valine, histidine and methionine is at least 12 wt %, based on total proteinaceous matter; and/or wherein the composition comprises leucine in free form, wherein the total amount of L-leucine provided by the proteinaceous matter amounts to at least 7 wt %, based on total proteinaceous matter.

2. The method according to claim 1, wherein the composition comprises vitamin B6 and/or vitamin B12.

3. The method according to claim 1, wherein the composition further comprises therapeutically effective amounts of one of more of uridine, cytidine and/or salts, phosphates, acyl derivatives and/or esters thereof.

4. The method according to claim 1, wherein the subject is an infant or child up to 18 years of age.

5. The method according to claim 1, wherein the composition further comprises therapeutic amounts of at least one antioxidant selected from the group consisting of selenium, vitamin C, vitamin E, and functional equivalents thereof.

6. The method according to claim 1, wherein the composition comprises selenium.

7. The method according to claim 1, wherein the sum of threonine, valine, histidine and methionine is between 15-60 wt %, based on total proteinaceous matter.

8. The method according to claim 1, wherein the composition comprises leucine in free form, and wherein the total amount of L-leucine provided by the proteinaceous matter amounts to between 9-20 wt %, based on total proteinaceous matter.

9. The method according to claim 1, wherein the composition comprises vitamin D and vitamin K, or functional equivalents thereof.

10. The method according to claim 1, wherein the composition further comprises therapeutically effective amounts of one of more of uridine and/or salts, phosphates, acyl derivatives and/or esters thereof.

11. A method for treating a subject suffering from or at increased risk of impaired recognition and/or working memory associated with PKU, wherein recognition and/or working memory is therapeutically improved, promoted, restored or maintained in the subject, wherein the method comprises administering to the subject a composition comprising therapeutic amounts of:
(i) at least one ω-3 polyunsaturated fatty acid (LCPUFA) selected from the group consisting of docosahexaenoic acid (DHA), eicosapentaenoic acid (EPA) and docosapentaenoic acid (DPA);
(ii) choline, a choline salt and/or choline ester;
(iii) at least one B vitamin selected from the group consisting of vitamin B6, vitamin B12, vitamin B9, and functional equivalents thereof;
(iv) at least one of vitamin D, vitamin K, and functional equivalents thereof; and
(v) proteinaceous matter which is essentially free of phenylalanine, and wherein the sum of threonine, valine, histidine and methionine is at least 12 wt %, based on total proteinaceous matter; and/or wherein the composition comprises leucine in free form, wherein the total amount of L-leucine provided by the proteinaceous matter amounts to at least 7 wt %, based on total proteinaceous matter.

12. The method according to claim 11, wherein the subject is an infant or child up to 18 years of age.

13. The method according to claim 11, wherein the composition comprises vitamin D and vitamin K, or functional equivalents thereof.

14. The method according to claim 11, wherein the composition further comprises therapeutically effective amounts of one of more of uridine and/or salts, phosphates, acyl derivatives and/or esters thereof.

15. A composition, comprising therapeutic amounts of:
   (i) at least one ω-3 polyunsaturated fatty acid (LCPUFA) selected from the group consisting of docosahexaenoic acid (DHA), eicosapentaenoic acid (EPA) and docosapentaenoic acid (DPA);
   (ii) choline, a choline salt and/or choline ester; and
   (iii) at least one B vitamin selected from the group consisting of vitamin B6, vitamin B12, vitamin B9, and functional equivalents thereof;
   (iv) at least one of vitamin D, vitamin K, and functional equivalents thereof; and
   (v) proteinaceous matter which is essentially free of phenylalanine, and wherein the sum of threonine, valine, histidine and methionine is at least 12 wt %, based on total proteinaceous matter; and/or wherein the composition comprises leucine in free form, wherein the total amount of L-leucine provided by the proteinaceous matter amounts to at least 7 wt %, based on total proteinaceous matter.

16. The composition according to claim 15, further comprising therapeutically effective amounts of one of more of uridine, cytidine and/or salts, phosphates, acyl derivatives and/or esters thereof.

17. The composition according to claim 15, wherein the sum of threonine, valine, histidine and methionine is between 15-60 wt %, based on total proteinaceous matter.

18. The composition according to claim 15, wherein the composition comprises leucine in free form, and wherein the total amount of L-leucine provided by the proteinaceous matter amounts to between 9-20 wt %, based on total proteinaceous matter.

19. The composition according to claim 15, wherein the composition comprises vitamin D and vitamin K, or functional equivalents thereof.

* * * * *